United States Patent [19]

Corey, Jr. et al.

[11] 3,985,868

[45] Oct. 12, 1976

[54] ASTHMA TREATMENT BY INHALATION OF MICRONIZED N,N-DIETHYL-4-METHYL-1-PIPERAZINECARBOXAMIDE PAMOATE

[75] Inventors: Howard Seebree Corey, Jr., New City; William Charles Barringer, Pearl River; Lloyd Frank Hansen, Campbell Hall, all of N.Y.

[73] Assignee: American Cyanamid Company, Stamford, Conn.

[22] Filed: Jan. 13, 1975

[21] Appl. No.: 540,735

Related U.S. Application Data

[62] Division of Ser. No. 374,174, June 27, 1973, Pat. No. 3,895,111.

[52] U.S. Cl. .................................. 424/45; 222/4; 222/395; 424/46; 424/250
[51] Int. Cl.² ................. A61K 9/14; A61K 31/495
[58] Field of Search ..................... 424/250, 45, 46

[56] References Cited

UNITED STATES PATENTS

| | | | |
|---|---|---|---|
| 3,012,555 | 12/1961 | Meshberg | 128/203 |
| 3,219,533 | 11/1965 | Mullins | 424/45 X |
| 3,282,781 | 11/1966 | Macek et al. | 424/45 |
| 3,457,350 | 7/1969 | Mallen | 424/250 |
| 3,491,135 | 1/1970 | Krueger et al. | 260/448 |
| 3,895,111 | 7/1975 | Corey et al. | 424/250 |

*Primary Examiner*—Leonard Schenkman
*Attorney, Agent, or Firm*—Samuel Branch Walker; Neal O. Willmann

[57] ABSTRACT

Asthma is effectively treated by inhalation of powder dispensed from an aerosol suspension of powdered N,N-diethyl-4-methyl-1-piperazinecarboxamide pamoate, which is dispersed as a fine powder, essentially below 10 microns in particle size, which gives an improved ratio of absorption in the lungs as compared to systemic absorption.

3 Claims, 5 Drawing Figures

ASTHMA TREATMENT BY INHALATION OF MICRONIZED N,N-DIETHYL-4-METHYL-1-PIPERAZINECARBOXAMIDE PAMOATE

CROSS-REFERENCE TO RELATED APPLICATIONS

This application is a division of application Ser. No. 374,174, filed June 27, 1973 which issued as U.S. Pat. No. 3,895,111 on July 15, 1975.

BACKGROUND OF THE INVENTION

Most of the medicaments for inhalation therapy have been dispensed as sprays from solutions either using a pressurized gas source for a separate solution in a spray device or as a self-contained gas source mixed with the medicament in a pressure dispensing container, frequently called an aerosol spray can.

Most commonly, the medicament is either a liquid, or dissolved in a solvent to be dispersed as a liquid, and if a volatile liquid is chosen, the solvent may evaporate to give an inhalable powder. Less commonly, the medicament is suspended as a powder in a propellant and dispersed as a dry aerosol directly. A major problem has been to secure effective dispersal in a desired particle size range. Patents and promotional literature are often unwarrantedly optimistic as to the effectiveness of dispersion.

For effective inhalation therapy where the drug is to be administered to the lower reaches of the lungs, it has been recognized that a particle size of the order of 0.5 microns to 10 microns is desired. Larger particles have a tendency to be deposited in the nasal or oral passages before the drug gets to the lung, and any effect on the lungs is by systemic absorption with the drug being circulated in the blood to the lungs. Sometimes the systemic effect of the drug on other organs is of dubious effectiveness or actually undesired, with what might be called topical application to the lungs being a preferred method of administration.

SUMMARY OF THE INVENTION

The present invention is based upon the discovery that micronized N,N-diethyl-4-methyl-1-piperazinecarboxamide pamoate can be effectively administered for the treatment of asthma by subdividing, suspending in a chlorofluoralkane propellant, preferably using ethanol as a dispersing aid and valve lubricant, by spraying under pressure through a decelerating and diluting chamber which delivers a powder predominantly in the particle size range of 5 microns to 1 micron, which is largely deposited in the lungs on inhalation and has the desired local physiological effect.

Even if the N,N-diethyl-4-methyl-1-piperazinecarboxamide pamoate be ground to a particle size of less than 10 microns, when suspended in the chlorofluoralkane for pressure dispensing, some of the particles tend to agglomerate or flocculate or impact in the mouth of the user, so a deceleration and dilution chamber in the system aids in administration.

As pamoic acid is a dibasic acid, either a mono or a bis salt may be formed with N,N-diethyl-4-methyl-1-piperazinecarboxamide. Either form or mixture thereof may be used. Free carboxylic groups may be neutralized to form non-toxic physiologically inert salts such as ammonium or alkali metal salts, such as sodium or potassium. The equimolar salt as the free acid has excellent handling characteristics, is easily prepared and dispersible in the preferred size range, and, hence, is a convenient and preferred form to use, but other forms are also useful.

DESCRIPTION OF THE PRIOR ART

U.S. Pat. No. 2,467,895, Kushner and Brancone, Apr. 19, 1949, "Piperazine Derivatives and Method of Preparing The Same", shows 1-methyl-4-piperazine-N,N-diethyl carboxamide, and its salts, which may also be named as 1-diethylcarbamyl-4-methyl-piperazine, commonly called diethylcarbamazine, and is sold as its dihydrogen citrate salt under the trademark HETRAZAN.

U.S. Pat. No. 3,457,350, Mallen, July 22, 1969, "Method Of Treating Asthma", shows the use of N,N-diethyl-4-methyl-1-piperazine carboxamide (commonly called diethylcarbamazine) for asthma. The dihydrogen citrate salt is disclosed specifically.

U.S. Pat. No. 3,491,135, Krueger, Barringer, and Henderson, Jan. 20, 1970, "Pamoates Of (3-Cyclohexyl-3-Hydroxy-3-Phenylpropyl) Triethylammonium Having Unobjectionable Flavors" teaches the use of pamoate salts of other therapeutic agents.

U.S. Pat. No. 2,992,645, Fowler, July 18, 1961, "disperser For Powders", in Column 2 has a table showing the effect of particle size on the zone of deposition of a powder in the respiratory tract. Powder sizes of 1 and 3 microns are shown to go deeply into the lungs.

U.S. Pat. No. 3,012,555, Meshberg, Dec. 12, 1961, "Dispensing Package For Material Under Pressure" shows an aerosol liquid dispenser with an operating spray button assembled to the valve stem, which button, with spray orifice, fits removably into an applicator nozzle.

U.S. Pat. No. 3,219,533, Mullins, Nov. 23, 1965, "Aerosol Solid Medicament In Propellant And Low-Level Ethanol Avoiding Higher-Level Ethanol Dispersed-Solid Reflocculation" shows steroids such as hydrocortisone, prednisolone and dexamethasone dispersed in the particle size range of 0.5 to 10 microns using 0.5 to 5.0% ethanol, for inhalation and opthalmic therapy.

It has now been found that the pamoate salts of N,N-diethyl-4-methyl-1-piperazinecarboxamide form a therapeutically effective form of N,N-diethyl-4-methyl-1-piperazinecarboxamide which when administered as a fine powder, preferably in the range of 0.5 to 10 microns, to the lungs is readily pharmacologically available in the lungs with the pamoic acid moiety having minimal or no side effects as a therapeutic agent, and serving to form a nonhygroscopic readily manipulated salt. The salt can be readily ground in a fluid energy mill, readily dispersed in the chlorofluoro-loweralkanes, frequently termed "Freons", which are volatile at room temperature. The pressurized container in a suitable dispenser dispenses the material in finely-divided form which has few particles larger than about 10 microns, and permits administration by inhalation through the mouth to the lungs, whereby the therapeutic effect of the N,N-diethyl-4-methyl-1-piperazinecarboxamide pamoate is primarily at the desired site, namely, in the lungs.

One such dispensing device is described below; although other devices may be used to dispense and disperse the powdered diethylcarbamazine pamoate of this invention, if the desired particle size range is obtained:

DRAWINGS

Figure 1:
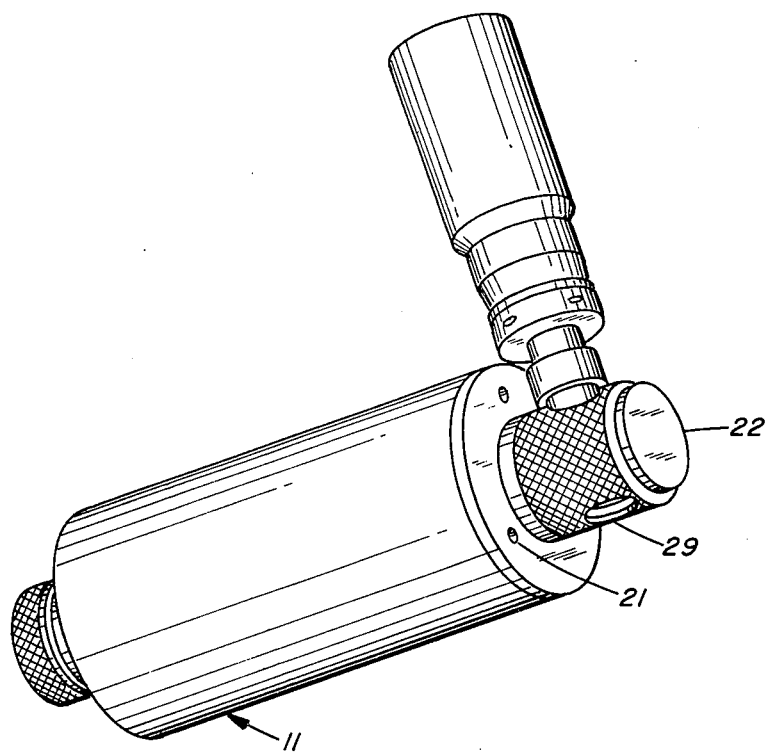
FIG. 1 is a pictorial view of the aerosol dispenser assembled in dose administering configuration.

As shown in FIG. 1, the biggest element of the aerosol dispenser is the deceleration chamber 11, preferably of a plastic such as polyethylene. The deceleration chamber has a cylindrical barrel 12 which conveniently may be about 2¾ inches in length and 1½ inches in internal diameter with a shell wall thickness of around 1/16 inch. At one end is a mouthpiece 13 conveniently about ⅞ inch in outside diameter and ⅝ inch long which is a size conveniently held in the lips of the user with the lips forming an essentially airtight seal with the mouthpiece. The mouthpiece is joined to the cylindrical barrel 12 by a chamber-to-mouthpiece flare 14. Conveniently, but not necessarily, the mouthpiece, the chamber-to-mouthpiece flare, and the cylindrical barrel are molded in one piece from a plastic such as linear polyethylene. This gives an economical method of manufacture and a smooth, easily cleanable working surface. A mouthpiece cap 15 fits removably on the mouthpiece in dust excluding relationship. The cap may slide on either interiorly or exteriorly with a finger friction fit. The term "finger friction fit" is used to note a frictional relationship which will hold pieces together under normal handling conditions, but may be readily disengaged or engaged by finger pressure only. The exterior surface of the mouthpiece cap may be roughened or knurled for easier grasping by the fingers. The edges of the mouthpiece cap and the mouthpiece may be "broken" or slightly rounded in accordance with conventional practice for ease in assembly, as may other edges. Either the mouthpiece or the mouthpiece cap may have small ribs of the order of 0.002 inch to reduce friction and ease engagement. By having such small raised portions or beads on frictionally engaging portions, the natural resilience of plastic such as polyethylene is utilized to give a frictional engagement which may be readily disengaged with the fingers without expensive requirements as to accuracy in sizing of the pieces. Similar assembly details may be used elsewhere in the present dispenser, and are conventional in the plastics molding art.

At the open end of the cylindrical barrel 12 is a container holder 16. The container holder is a multifunctional element. A holder flange 17 fits across the open end of the cylindrical barrel 12. A positioning sleeve 18 engages the end of the cylindrical barrel 12. Conveniently, but not necessarily, the positioning sleeve fits interiorly of the cylindrical barrel 12 with a friction fit and the positioning sleeve is long enough to prevent accidental disengagement but permit ready removal of the container holder 16. Conveniently, but not necessarily, the positioning sleeve 18 extends from the holder flange 17 so that its resilience permits finger frictional engagement with the normal accuracy of molding parts. A container holding sleeve 19 extends interiorly from the holder flange 17 and is of a size to fit around, retain, and position an aerosol container 20. Conveniently, but not necessarily, the aerosol container 20 is of stainless steel or aluminum to hold high pressure aerosol propellants. The container holding sleeve is long enough and of a size to position and retain the aerosol container assembly inside and axially of the deceleration chamber 11 during storage and transportation phases of using the device, and permits ready disengagement from the aerosol container 20 at the time of administration.

Through the holder flange extend one or more air vents 21 which provide for the introduction of diluent air during use. Three vents, each ⅛ inch diameter, give good results.

Extending exteriorly from the holder flange 17 is a button holder 22. The button holder is hollow, has a closed end opposite to the holder flange, and has therein an indexing port 23 which is of a size and shape to hold an aerosol actuating button 24, which is described in more detail below. Because the aerosol actuating button is to be oriented, the shape of the indexing port 23 is such as to match with the actuating button 24 and hold the actuating button in an oriented relationship. As shown, the actuating button is cylindrical with a flat side 25 which flat side cooperates with an indexing port flat 26 so that the spray is directed axially of the deceleration chamber. Conveniently, but not necessarily, the button holder is formed with two indexing ports 23 in diametrically opposed relationship so that the actuating button 24 can be inserted from either side and the other port serves such as an additional air inlet. At the end of the button holder 22 away from the holder flange 17 is a retaining bead 27 which conveniently extends up about 5/1000ths of an inch above the exterior cylindrical surface of the button holder. A protective sleeve 28 fits in light frictional engagement over and on the exterior surface of the button holder. Being made of plastic, there is sufficient resilience that the protective sleeve 28 may be easily forced over the retaining bead 27 into position and is not readily removed so that it is retained in place during the useful life of the dispenser. The protective sleeve has button apertures 29 to permit the sleeve 28 to be rotated so that the button apertures 29 index with the indexing ports and permit the button to be inserted therethrough and yet can be rotated through about 90° to protect the assembly from the entrance of dust and dirt during storage and transportation.

Figure 2:
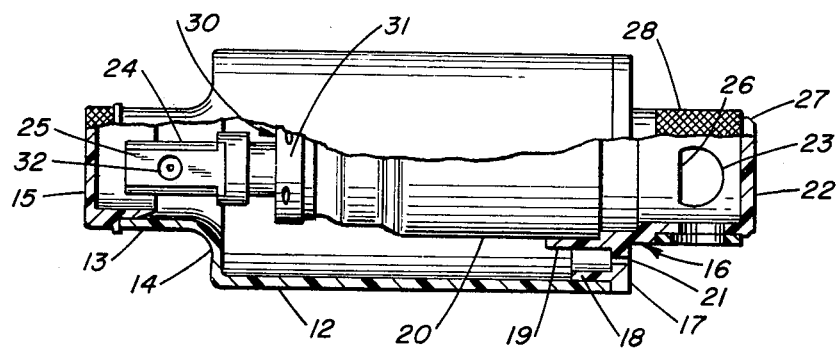
FIG. 2 is a view in partial section showing the dispenser in the storage and transportation configuration.

In FIG. 2 is shown the dispenser in the carrying configuration for storage and transportation in which the aerosol container 20 is held in the container holding sleeve 19 interiorly of the cylindrical barrel of the deceleration chamber.

The aerosol container 20 is closed with a valve assembly 30 which includes a ferrule 31 to hold the valve in position and from which valve assembly extends the actuating button 24.

Figure 3:
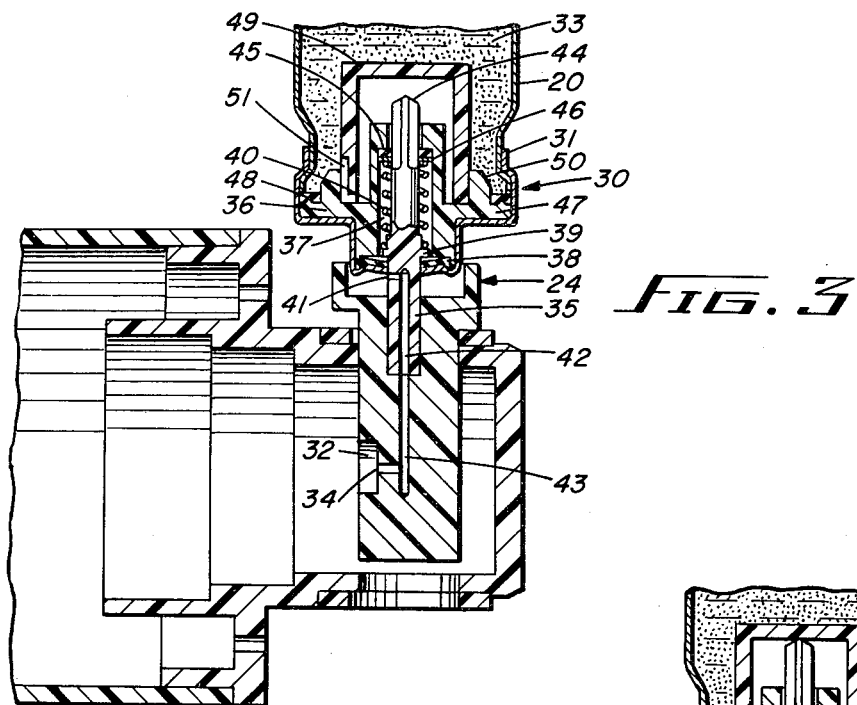
FIG. 3 is an enlarged view in section showing the valve assembled to the expansion chamber cover and particularly, an anti-drain tank to insure that the metering valve is continuously immersed in the propellant and, thus, protected from partial draining and resulting irregular dosages.

As shown in FIG. 3, at the time of use, the mouthpiece cap 15 is removed, the holder flange 17 removed from the other end of the cylindrical barrel, the aerosol container 20 is removed from the container holding sleeve 19, the protective sleeve 28 rotated until the button apertures 29 index with the indexing port 23, and assembled in dose administering configuration by inserting the actuating button 24 through the button aperture 29 into one of the indexing ports 13 so that the spray port 32 is axial and concentric with the cylindrical barrel 12 of the deceleration chamber, so that the discharge from the aerosol container is symmetrical with respect to the deceleration chamber.

As shown in FIG. 3, in the dose administering position the aerosol container 20 extends upwards so that the medicament in propellant 33 is drawn by gravity against the valve assembly 30.

The actuating button 24 has a spray port 32 which is conveniently counterbored into the button and has a spray orifice 34 through which the medicament in propellant is discharged. This spray orifice may either be formed integral with the spray button or a separate metallic insert may be used. Both are conventional constructions. The spray orifice should have a diameter such that the discharged dose is disbursed in finely divided form as a cone on exit from the spray orifice.

An orifice of about 0.015 to 0.018 inch gives a good spray pattern.

The actuating button 24 fits snugly on the end of a valve stem 35 which extends into the valve body 36. The valve body 36 has therein a metering chamber 37 in which the valve stem 35 is slidably mounted. Between the valve body and the ferrule 31 is a metering gasket 38 which performs the dual function of serving as a seal against loss of propellant when the valve stem collar 39 presses against the metering gasket, and acts as a ring seal around the valve stem 35 so that as the valve stem is depressed against the valve spring 40, the metering port 41 in the valve stem passes the metering gasket and permits the contents of the metering chamber to pass through the metering port 41, the axial valve stem bore 42, extending through the valve stem, into the discharge passage 43 in the actuating button 24 to the spray orifice 34. At the inner end of the valve stem 35 are charging flutes 44. These cooperate with a charging gasket 45 which is held against the lower end of the metering chamber by a stainless steel valve stem washer 46 which, in turn, is held against the bottom of the metering chamber 37 by the valve spring 40. In operation, as the valve stem 35 is depressed, the valve stem 35 passes through the charging gasket 45 so that the charging flutes pass through the charging gasket and the full diameter of the valve stem 35 seals against the charging gasket 45 so that the metering chamber is filled and closed at the inner end before the metering port 41 passes the metering gasket 38 which permits the contents of the metering chamber to discharge through the metering port 41, the axial valve stem bore 42, the discharge passage 43, and the spray orifice 34.

Figure 4:
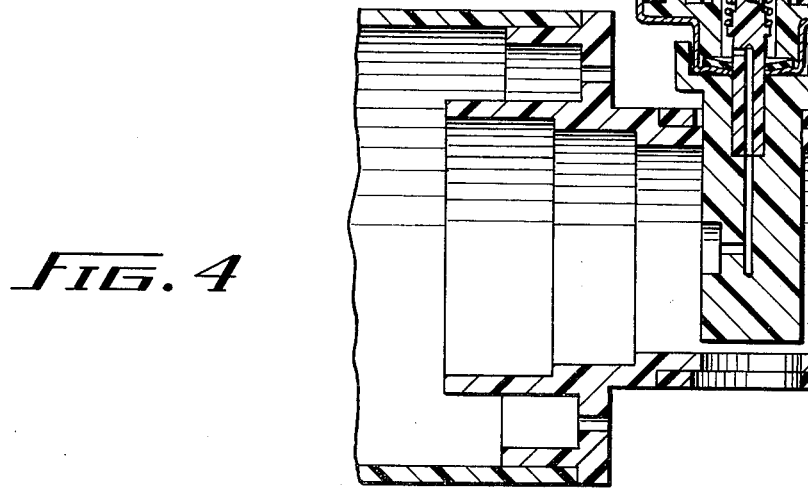
FIG. 4 shows the same valve assembly in compressed position after a dose in which the valve stem has been depressed.
Figure 5:
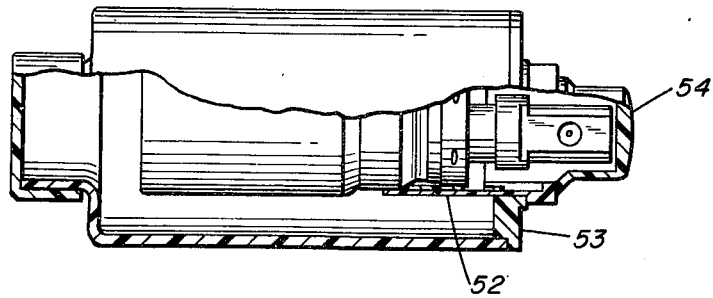
FIG. 5 is a second configuration in which the actuating button fits into a movable applicator nozzle for storage.

FIG. 4 shows the actuating button 24 in depressed position with the valve in the discharge position.

When pressure on the actuating button 24 is released, the valve stem 35 is pushed outwardly by the valve spring 40 so that the metering port 41 passes the metering gasket 38 which closes discharge from the metering chamber, and later the charging flutes 44 pass the charging gasket 45 permitting the propellant containing the medicament to flow through the charging flutes 44 and again fill the metering chamber 37.

The valve body 36 has a valve body flange 47 which covers the end of the aerosol container 20 and is sealed thereto by a container gasket 48. The ferrule 31 holds the assembly in position against the end of the aerosol container 20 by the ferrule 31 being swaged against the stainless steel or aluminum aerosol container 20.

The above construction for a metering valve is one type of metering valve. other conventional types of metering valves may be used.

Because the metering valve discharges a comparatively small charge, for instance about 50 microliters per actuation is a convenient commercial size, and each discharge has a volume of about that of a small drop of water, it is important that the metering chamber be completely filled before each actuation and that the metering chamber be prevented from draining back into the aerosol container between actuations. This loss of charge or loss of prime is prevented by an anti-drain tank 49. The anti-drain tank 49 fits into a flange sleeve 50 on the valve body flange 47 which flange sleeve 50 has an interior cylindrical surface against which the anti-drain tank 49 is a snug friction fit. In the periphery of the anti-drain tank 49 and between the anti-drain tank and the flange sleeve 50 is a charging passage 51 which provides for refilling of the anti-drain tank from the main body of the medicament in propellant in the aerosol container.

To protect against accidental disengagement of the anti-drain tank as, for example, by dropping the aerosol container on the floor during use, the anti-drain tank is sonically welded into position using an ultrasonic seal in which ultrasonic energy is passed through the flange sleeve to the anti-drain tank. As the energy passes through, there is a discontinuity between the anti-drain tank and the flange sleeve so that energy is reflected and refracted causing dissipation of ultrasonic energy which reappears as heat which melts and thereby seals the anti-drain tank to the flange sleeve. By such ultrasonic sealing, the assembly is economical and effective. When so sealed, the anti-drain tank remains in position under any use or abuse that does not damage the aerosol container itself.

Because of the nature of the propellant composition, when the actuating button is depressed with the aerosol container in dispensing position, the contents of the metering chamber are discharged and as the actuating button is released, a new charge is drawn from the anti-drain tank into the metering chamber and the anti-drain tank is refilled through the charging passage 51. The anti-drain tank remains filled with the propellant containing the medicament independent of the orientation of the aerosol container. Thus, a predictable, uniform, accurate dosage is dispensed with each actuation of the actuating button.

By keeping the fluted end of the valve stem immersed in liquid propellant at all times, the homogeneity of the solid finely divided medicament in the propellant is maintained more uniformly, and more consistent uniform doses are dispersed. The use of a plastic anti-drain tank appears to aid in neutralizing electrical charges which would otherwise build up in the system. With a stainless steel aerosol container 20, the periphery of the propellant charge is effectively at a single potential, but the propellant can act as a dielectric so that the individual particles of medicament become charged and affect their dispersion and discharge rate. With the anti-drain tank, the effect of the stainless steel container is at least in part neutralized so that static effects are reduced or minimized permitting more uniform charge characteristics.

In the absence of the anti-drain tank, the first twenty-five per cent of discharge doses are found to be higher than the last 25 per cent so that the user is receiving more medication than anticipated from the new dispenser and less than anticipated from the nearly empty dispenser. With the present anti-drain tank, the variation in charges are minimized so that the user is obtaining a more reliably uniform dosage of the medicament.

It is difficult to measure the effect of electrical charges within the aerosol container and in the deceleration chamber but independent of the theoretical and scientific background for explaining uniformity of charge, it is found that with the present anti-drain tank, more uniform dosages are dispensed and with the deceleration chamber in which the mouthpiece has less than half the cross sectional area of the cylindrical barrel, and the length of the cylindrical barrel is less than twice its diameter, the individual dosages of medicament in propellant are dispersed into the deceleration chamber and lose the jet velocity imparted by the propellant spray. If any particles still retain velocity, they either impinge or are retained by the walls of the deceleration chamber or are bounced away from the walls so that a dispersed powder charge is formed which is mixed with additional diluent air and inhaled, as the user inhales the finely divided medicament through the mouthpiece. A large portion of the medicament which would otherwise be deposited in the mouth of the user and, hence, absorbed systemically, are deposited on the walls of the deceleration chamber.

Even though the medicament may be fairly expensive, the dosages are so small that about a 25 to 50% loss in the deceleration chamber is a highly acceptable loss as compared with the advantages of consistency and uniformity of the dose which is administered to the patient.

With many drugs it is very important that the desired quantity be administered to the user. Uniformity is important so that the physician administering knows what adjustments in dosage level need be made depending on the response of the user.

In FIG. 5 is shown a modification of the aerosol dispenser system in which the container holding sleeve of the type shown in Meshberg, U.S. Pat. No. 3,012,555, supra, is used with an applicator nozzle 52 fitting in the holder flange 53 with the bottom end of the aerosol container fitting into the applicator nozzle. Slidably fitting in the other end of the applicator nozzle is a button holding slide 54 which can be pressed inward for sealing or pulled outward to hold the actuating button in operating position. The details of this construction are shown in said U.S. Pat. No. 3,012,555.

Other configurations can be used providing that the deceleration chamber is large enough to decelerate the dispensed aerosol charge and permit the inhalation velocity from the inhalation of the user to be the sole factor in controlling the rate of administration at the time of use. With a metering trap holding about 50 microliters of material, the energy of discharge is completely dissipated in the deceleration trap and a fine aerosol, almost a smoke, is formed of the drug to be administered, and this fine aerosol is inhaled into the lungs.

For Applicant's purpose, a particle size range from about 0.5 microns to 10 microns gives good results. Particles larger than about 10 microns are too apt to be deposited in the mouth or the throat of the user to be preferred for inhalation therapy. A few particles in this size range are usually not deleterious, but contribute disproportionately to systemic absorption rather than through the lungs.

In use, because part of the medicament deposits on the walls of the deceleration chamber, the chamber should be washed occasionally.

To insure adequate dispersion of the powdered medicament in the propellant, a comparatively high pressure propellant system is preferred. Dichlorodifluoromethane (Freon 12) which has a pressure of about 80 pounds per square inch absolute at room temperature gives good results. A stainless steel or aluminum container is preferred for such pressures to avoid damage from breakage. Glass containers, or plastic containers, or a plastic covered and protected glass container may be used, but these are more conventional at lower pressures, of the order of 30 to 50 pounds per square inch gage.

A plastic valve stem is preferred to metal, as the plastic valve stem is less subject to binding or sticking from powder being packed around it. A small amount of alcohol, about 1% to 10%, functions as a lubricant to keep valve action reliable.

The following examples show the preparation of salts of N,N-diethyl-4-methyl-1-piperazinecarboxamide with pamoic acid. Usually, a mole to mole ratio is preferred because it has desirable physical properties and is easy to prepare. As pamoic acid is dicarboxylic, a greater than one molar ratio of N,N-diethyl-4-methyl-1-piperazinecarboxamide to pamoic acid may be used.

During purification, it is convenient to dissolve the N,N-diethyl-4-methyl-1-piperazinecarboxamide in an acid form in a solvent which permits the removal of impurities and recrystallize as a pure N,N-diethyl-4-methyl-1-piperazinecarboxamide pamoate.

EXAMPLE I

Diethylcarbamazine Pamoate

At room temperature, a 2.0 gm (0.005 mole) portion of diethylcarbamazine (N,N-diethyl-4-methyl-1-piperazinecarboxamide) dihydrogen citrate is dissolved in 20 ml. of water. A 2.16 gm (0.005 mole) portion of the disodium salt of pamoic acid is added. A crystalline precipitate separates immediately, but after standing for about 5 hours at room temperature this disappears and is replaced by an amorphous precipitate. On further standing for 2 days, the amorphous precipitate gradually changes to a crystalline form which is collected and dried yielding 2.5 gm.

Repetition of this procedure, with the exception that the sodium pamoate is added as an aqueous solution rather than a dry powder, results in the immediate precipitation of an amorphous solid that gradually crystallizes over a two day period. The solid is collected and air dried yielding 2.7 gm, M.P. 215° C. with decomposition.

Calculated: C, 67.44; H, 6.35; N, 7.15. Found: C, 66.90; H, 6.26; N, 7.05.

EXAMPLE II

Diethylcarbamazine Pamoate From Pamoic Acid

At room temperature, 15.4 Kg. (32.4 mole) of technical grade disodium pamoate monohydrate is added to 175 liters of methanol in a 100 gallon stainless steel kettle, and the mixture stirred until maximum, but not complete, solution is obtained. 1.5 Kg. of activated charcoal and 1.5 Kg. of diatomaceous earth are added and the mixture is stirred for one hour. The mixture is filtered through diatomaceous earth. The cake is washed with three 2 liter portions of methanol. The filtrate and washes are charged in a 100 gallon glass lined kettle, 21 liters of water added, and 10.9 liters (130 moles) of concentrated hydrochloric acid is added fairly rapidly. A bright yellow solid precipitates immediately. Stirring is continued at room temperature for 1½ hours. Free pamoic acid is recovered by filtration and washed with three 20 liter portions of water. The cake is slurried with about 80 liters of water for 1 hour, solids filtered off, the solids washed with three 2 liter portions of water and then with three 4 liter portions of methanol. The solid is then dried for two days at 50°–55° C. The crude pamoic acid (11.8 Kg.) is dissolved in 61 liters of dimethylformamide at 85°–90° C. Two pounds of diatomaceous earth are added and the mixture is stirred for ½ hour before filtering through pre-heated funnels. The cake is washed with three 3 liter portions of dimethylformamide. The filtrate is added to 70 liters of water in a 50 gallon glass lined kettle. An additional 20 liters of water is added and the resulting mixture is stirred for 1½ hours while being cooled to below 25° C. The purified pamoic acid is filtered off, pressed dry and then washed with three 6 liter portions of water followed by three 4 liter portions of methanol. The pamoic acid is dried to a constant weight of 10.8 Kg. (86% based on 95% real starting disodium salt).

A 10.1 Kg. (25.8 moles) portion of diethylcarbamazine dihydrogen citrate is dissolved in 80 liters of water and the solution is filtered.

A 1.96 Kg. (49.0 moles) portion of sodium hydroxide is dissolved in 100 liters of water and 10.0 Kg. (25.8 moles) of purified pamoic acid, prepared as described in this example, is added. The pamoic acid-sodium hydroxide mixture is stirred for ½ hour, two pounds of diatomaceous earth is added, stirring is continued for 1 hour and the mixture is clarified by filtration.

The filtrate is charged in a 100 gallon glass lined kettle, stirred and the diethylcarbamazine citrate solution is added as rapidly as convenient. A very thick cream-colored precipitate forms immediately. Forty liters of water is added. After 1 hour of stirring the mixture thins out considerably. Stirring is continued for 1 more hour. The product is collected by filtration and washed with three 15 liter portions of water. The material is dried at 50°–55° C., and then micro-milled twice in a fluid energy mill to give 13.5 Kg. of product. A 10.8 Kg. portion of this diethylcarbamazine pamoate is dissolved in a mixture of 25 liters of dimethylsulfoxide and 50 liters of methanol at 65° C. The hazy solution is filtered through diatomaceous earth and the cake is washed with three 4 liter portions of methanol. The filtrate and washes are charged in a 50 gallon glass lined kettle and warmed to dissolve any separated material. Forty liters of methanol are added and the solution is chilled to and maintained at 0° C±4° C. overnight. The product is filtered off and washed three times with 1.5 liters of methanol. After drying at 45°–50° C. the material is micro-milled yielding 8.0 Kg. of diethylcarbamazine pamoate(N,N-diethyl-4-methyl-1-piperazinecarboxamide pamoate)(equimolar) having 90% or more of the particles 10 microns or less in size.

EXAMPLE III

To a stirred suspension of 50.5 mg (0.13 mole) of purified pamoic acid in 400 ml of acetone heated to 50° C. there is added 53.0 gm (0.27 mole) of diethylcarbamazine dihydrogen citrate. The resulting clear yellow solution is allowed to cool to room temperature and is then filtered. The filtrate is concentrated to dryness in vacuo at 50° C. and the resulting product is dried in vacuo at 75°–80° C. for 16 hours yielding 102.0 gm of bis-(N,N-diethyl-4-methyl-1-piperazine carboxamide) pamoate as a yellow amorphous powder, M.P. 101°–105° C.

| Analysis: Calculated: $C_{43}H_{58}N_6O_8$ (787) Found: | C, 65.62; H, 7.44; N, 10.68 C, 65.22; H, 7.79; N, 10.80 |
|---|---|

EXAMPLE IV

N,N-diethyl-4-methyl-1-piperazinecarboxamide pamoate was passed through a fluid energy pulverizing mill and micronized to 0.5 to 10 microns, with 90% by weight being in the range of 1 to 5 microns. 300 milligrams thereof in dry form were introduced into a 19 milliliter stainless steel container adapted to be fitted with an aerosol metering spray nozzle, and thereto was added 0.75 grams of anhydrous ethanol. Chilled (−40° C) dichlorodifluoro methane was added from a pressure tank to the open container which by evaporative cooling rapidly chilled the container and its contents, enough being added that the container held 15 grams of dichlorofluoromethane, after which the container was closed with a metering valve, and the metering valve sealed in place.

A metering valve was used which discharged 50 microliters of contents per actuation which gives 1.3 milligrams of N,N-diethyl-4-methyl-1-piperazinecarboxamide pamoate per actuation with 65 milligrams of dichlorofluoromethane and 3.25 milligrams of ethanol being simultaneously dispensed. These are volatile and become mixed with enough air so as to have minimal or no physiological activity.

Depending upon the degree of severity of an asthmatic attack, one or more actuations inhaled bring relief. The inhalation administration gives a rapid and effective method of administration which is more rapidly effective than systemic administration.

The N,N-diethyl-4-methyl-1-piperazinecarboxamide pamoate is more effective for prophylactic or long term treatment than for instant relief. Other drugs are preferred for very rapid relief during an asthmatic attack. The present N,N-diethyl-4-methyl-1-piperazinecarboxamide pamoate in doses of from about 0.5 to 30 milligrams of diethylcarbamazine equivalent administered three time a day, the dosage level being adapted to the patient, and the intensity of therapy required, gives good long term control of many asthmatic conditions.

Because the diethylcarbamazine pamoate is administered directly to the lungs, a smaller dosage, as the diethylcarbamazine, is normally required for effective relief than if administered systemically, i.e., orally, with the circulatory system being utilized to carry the medicament to the lungs.

| INDEX OF PARTS | |
|---|---|
| 11. deceleration chamber | 41. metering port |

-continued

| INDEX OF PARTS | |
|---|---|
| 12. cylindrical barrel | 42. axial valve stem bore |
| 13. mouthpiece | 43. discharge passage |
| 14. mouthpiece-to-chamber flare | 44. charging flutes |
| 15. mouthpiece cap | 45. charging gasket |
| 16. container holder | 46. valve stem washer |
| 17. holder flange | 47. valve body flange |
| 18. positioning sleeve | 48. container gasket |
| 19. container holding sleeve | 49. anti-drain tank |
| 20. aerosol container | 50. flange sleeve |
| 21. air vents | 51. charging passage |
| 22. button holder | 52. applicator nozzle |
| 23. indexing port | 53. holder flange |
| 24. actuating button | 54. button holding slide |
| 25. flat side | |
| 26. indexing port flat | |
| 27. retaining bead | |
| 28. protective sleeve | |
| 29. button apertures | |
| 30. valve assembly | |
| 31. ferrule | |
| 32. spray port | |
| 33. medicament in propellant | |
| 34. spray orifice | |
| 35. valve stem | |
| 36. valve body | |
| 37. metering chamber | |
| 38. metering gasket | |
| 39. valve stem collar | |
| 40. valve spring | |

We claim:

1. A pressurized dispenser for the treatment of asthma containing a suspension consisting essentially of an effective amount of N,N-diethyl-4-methyl-1-piperazinecarboxamide pamoate having a particle size range of 0.5 microns to 10 microns, about 5% by weight of ethanol and a propelling amount of a low boiling chlorofluoalkane in a container having a metering valve.

2. The dispenser of claim 1 in which the propellant is dichlorofluoromethane and the container is stainless steel.

3. The dispenser of claim 1 in which the propellant is dichlorofluoromethane and the container is aluminum.

* * * * *